(12) United States Patent
Cvetanovic

(10) Patent No.: US 7,802,577 B2
(45) Date of Patent: Sep. 28, 2010

(54) HARNESS FOR STRETCHING THE PENIS

(76) Inventor: Miodrag Cvetanovic, Beogradska 177, 11224 Beograd - Vrcin (RS)

( * ) Notice: Subject to any disclaimer, the term of this patent is extended or adjusted under 35 U.S.C. 154(b) by 71 days.

(21) Appl. No.: 12/218,943

(22) Filed: Jul. 18, 2008

(65) Prior Publication Data

US 2008/0276944 A1    Nov. 13, 2008

(30) Foreign Application Priority Data

Jan. 19, 2006    (YU) .................................. 2006/0030

(51) Int. Cl.
*A61G 15/00*    (2006.01)
*A61B 19/00*    (2006.01)
*A61F 5/31*     (2006.01)
*A61F 5/00*     (2006.01)

(52) U.S. Cl. ..................... 128/845; 128/869; 128/876; 128/883; 602/32; 600/38; 600/41

(58) Field of Classification Search ............. 600/38–41; 128/845, 869, 876, 883, 885, 917, 918; 602/32, 602/36, 38

See application file for complete search history.

(56) References Cited

U.S. PATENT DOCUMENTS

| 764,801 | A | * | 7/1904 | Emerson | 600/39 |
|---|---|---|---|---|---|
| 853,410 | A | * | 5/1907 | Huebner | 600/39 |
| 1,462,000 | A | * | 7/1923 | Bennett | 600/39 |
| 3,920,007 | A | * | 11/1975 | Line | 600/39 |
| 4,381,000 | A | * | 4/1983 | Duncan | 600/39 |
| 4,440,183 | A | * | 4/1984 | Miller | 600/41 |
| 4,449,521 | A | * | 5/1984 | Panzer | 600/39 |
| 4,672,954 | A | * | 6/1987 | Panzer | 600/39 |
| 5,599,275 | A |   | 2/1997 | France | |
| 5,728,043 | A | * | 3/1998 | Yong | 600/39 |
| 5,800,340 | A | * | 9/1998 | Gekhter et al. | 600/39 |
| 5,893,827 | A | * | 4/1999 | Jaquez et al. | 600/38 |
| 6,033,374 | A | * | 3/2000 | Miller, Jr. | 602/36 |
| 6,186,943 | B1 | * | 2/2001 | Pan | 600/39 |
| 6,416,460 | B1 | * | 7/2002 | Jochum | 600/39 |
| 6,579,229 | B1 | * | 6/2003 | Nan | 600/38 |
| 7,086,998 | B2 | * | 8/2006 | Dana, III | 482/105 |
| D528,659 | S | * | 9/2006 | Cherfas et al. | D24/190 |
| 7,276,040 | B2 | * | 10/2007 | Gomez-de-Diego | 602/36 |

(Continued)

FOREIGN PATENT DOCUMENTS

CA    2 444 663    A1    3/2005

(Continued)

*Primary Examiner*—Patricia M Bianco
*Assistant Examiner*—Brandon Jackson
(74) *Attorney, Agent, or Firm*—Ober, Kaler, Grimes & Shriver; Royal W. Craig

(57) ABSTRACT

A harness for stretching the penis, includes a belt for encircling the waist of the user, with a fastening mechanism secured to a rear part of the belt. A first tractive means applies tractive forces at the base of the penis of a user of the harness, and is secured to the belt via the fastening mechanism. A second tractive means applies tractive forces at the edge of the head of the penis of a user of the harness, and is also secured to the belt via the fastening mechanism. The first tractive means and the second tractive means apply a stretching force to the penis of the user of the harness.

14 Claims, 3 Drawing Sheets

U.S. PATENT DOCUMENTS

| | | | |
|---|---|---|---|
| 7,578,785 B2 * | 8/2009 | Suchy et al. ............ 600/38 |
| 2005/0101452 A1 | 5/2005 | Dana |

FOREIGN PATENT DOCUMENTS

| | | |
|---|---|---|
| DE | 19620719 | 12/1996 |
| DE | 19915407 | 11/2000 |
| DE | 200 20 135 U1 | 2/2001 |
| EP | 0370932 | 5/1990 |
| EP | 0814733 | 1/1998 |
| WO | WO 9728764 | 8/1997 |
| WO | WO 9918897 | 4/1999 |

* cited by examiner

US 7,802,577 B2

HARNESS FOR STRETCHING THE PENIS

CROSS-REFERENCE TO RELATED APPLICATION

This application claims priority to International Application No. PCT/RS2007/000001 filed on 18 Jan. 2007, incorporated herein by reference.

BACKGROUND OF THE INVENTION

Numerous attempts have been made in order to solve the problem of phallus elongating and enlarging. The following art illustrates the present state of this field: Jorn (EP0814733), Jakob (WO9728764), Heinz-Guenther (DE19915407 and DE19620719), Daniel (U.S. Pat. No. 5,599,275), Didier (EP0370932) etc, all describe mechanical devices for stretching the penis by using mechanical and/or gravitational forces, while Roland (U.S. Pat. No. 5,836,864) uses the same forces, adding a vacuum in for the same purpose.

Known devices present various drawbacks. First, they are of limited effectiveness as they are not designed for whole-day use. Mechanical parts of known devices are made of rigid, inflexible materials that are unsuitable for contact with sensitive body parts during movement, and relatively uncomfortable for use. The bulky size of most known devices renders them very noticeable under clothing. Most known devices fail to effectively solve the problem of fast and easy stretching force adjustment. These and other shortcomings limit these apparatuses only for home use, i.e. for conditions in which the user's privacy is insured, contributing to their low efficiency. It has been found that elongation and enlargement of the penis requires a man to wear these devices constantly and for a long period of time (e.g. 1 year, 6-8 hours each day for 2-3 cm gain approximately). Consequently, one of the paramount design considerations for such devices is to make it comfortable and practical for use in any situation (walking, sitting on work, car driving, bus riding, physical work, physical activities and sports etc.). As can bee seen from the foregoing, the need exists for a harness for stretching a human penis that is comfortable and practical for a long time and whole-day use, for stretching a human penis of any size, with the possibility of attaining strong tractive forces, and with the possibility of fast and easy regulation of these forces.

SUMMARY OF THE INVENTION

The present invention provides a harness for stretching the penis comprises a belt, adapted to be worn around one's waist, connected at the rear side via small rotating snap-hooks with two inextensible cinching straps The straps each have a pair of half-rings for length adjustment. One strap on its lower end carries an adjustable rope loop to be placed around penis base. A second strap has a lower end connected, via an L-shaped connecting member, a flexible, adjustable loop encircling and tightened around the penis next to the penis head. Tightening of the straps provides permanent penis stretching force. This force, over a sufficiently long time, provides penis elongation and enlargement by the process of tissue mass increasing (a process which has for a long time been very well known to many primitive tribes). The provided harness is fabricated from flexible, human-body-friendly materials, do not contain bulky rigid parts and is therefore easy to wear and to bear. The harness is not readily noticeable under the trousers, shorts, boxers etc. While using it one can freely walk, do everyday activities, work, drive a car, even run, swim and do many other activities. Furthermore, a man can easily and quickly adjust stretching force on straps using adequate his fingers either over the clothing or in his pockets (even while walking, without stopping). By this harness is possible to provide heavy traction on penis, due to it's construction and due to a fact it is made of strong inextensible band at the rear side of the belt, of inextensible cinching straps and of very low elastic rope loop (the only needed-to-be flexible part is silicone i.e. rubber loop), providing this way the harness can be used for stretching the penis of any (even big) size. Minimal size (the same minimal size for all sizes of the peruses), weight and single-part feature of L-shaped connecting member facilitate a harness to be "imperceptible" while in use, while U-shaped aperture on said member provides a wide range of angles and positions penis can be stretched in. Comfortability of the harness is further provided with possibility of easy changing of the sides of the cinching straps (i.e. change of penis placement and stretching side). Comfortability is also conduced with fast-release function of both rope and elastic loops in order to prevent any kind of pain arising and side-effects. This harness is very easy to disassemble and to wash. Regarding to durable materials harness is made of, it can be used for years. This and other features and advantages of the present invention will become apparent from the following more detailed description taken in conjunction with the accompanying drawings.

BRIEF DESCRIPTION OF THE DRAWINGS

The accompanying drawings illustrate the present invention. In such drawings.

DETAILED DESCRIPTION OF THE INVENTION

Figure 1:
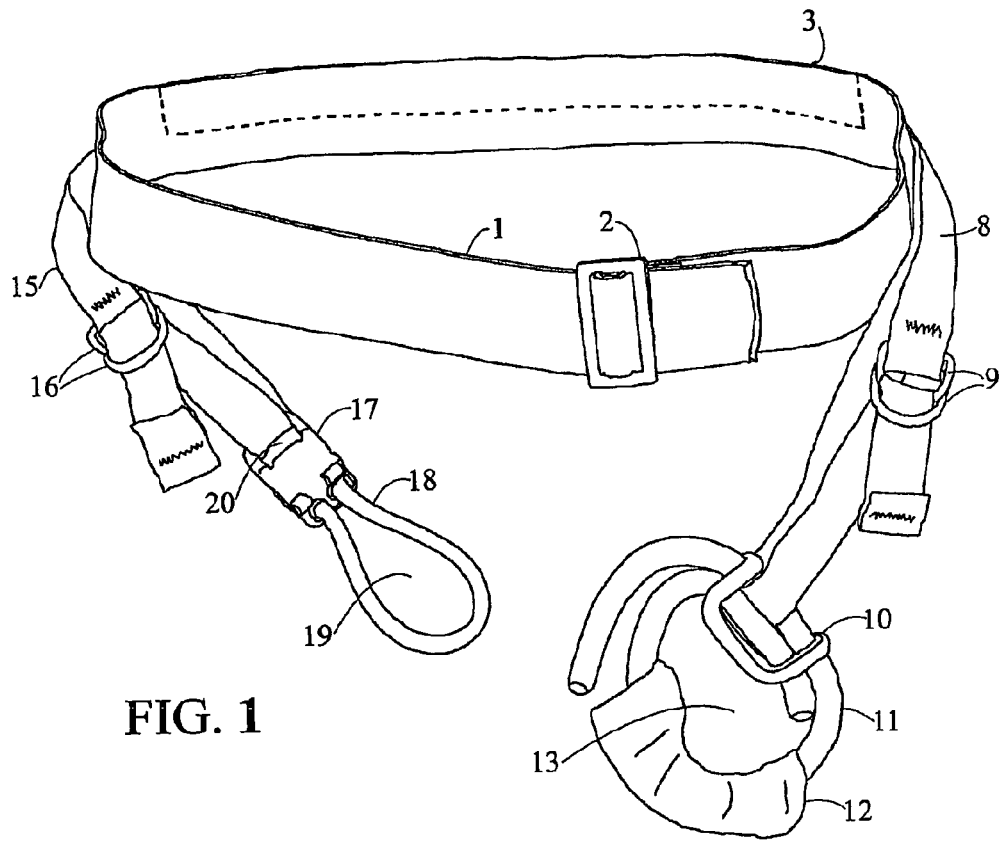
FIG. 1 is a view in front elevation of the present invention.
Figure 2:
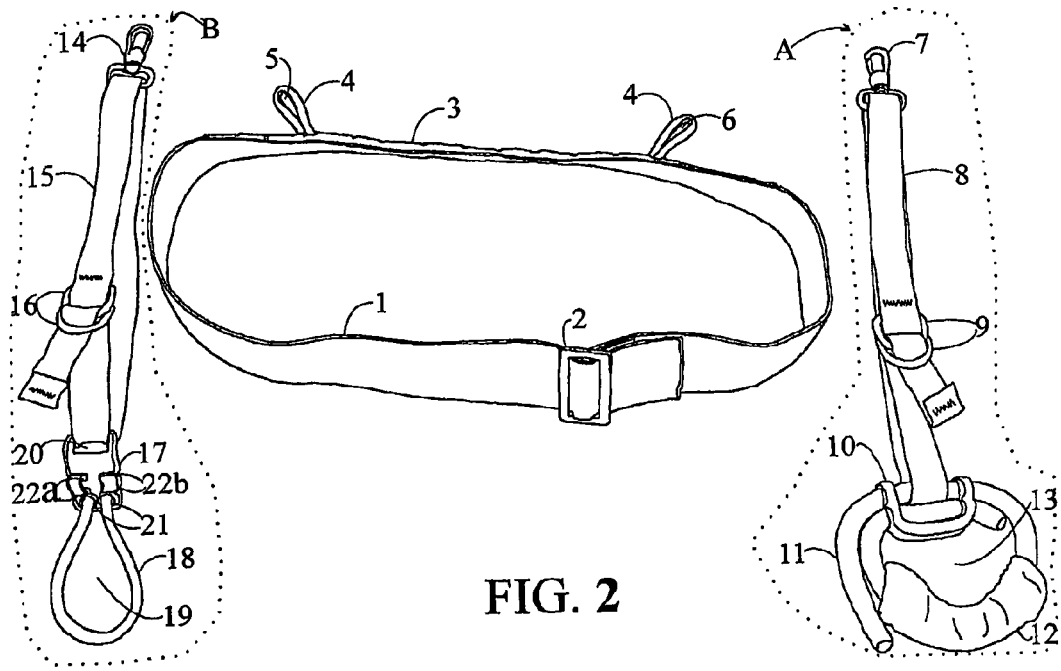
FIG. 2 is a view in front elevation of present invention disassembled on its 3 subsystems.
Figure 3:
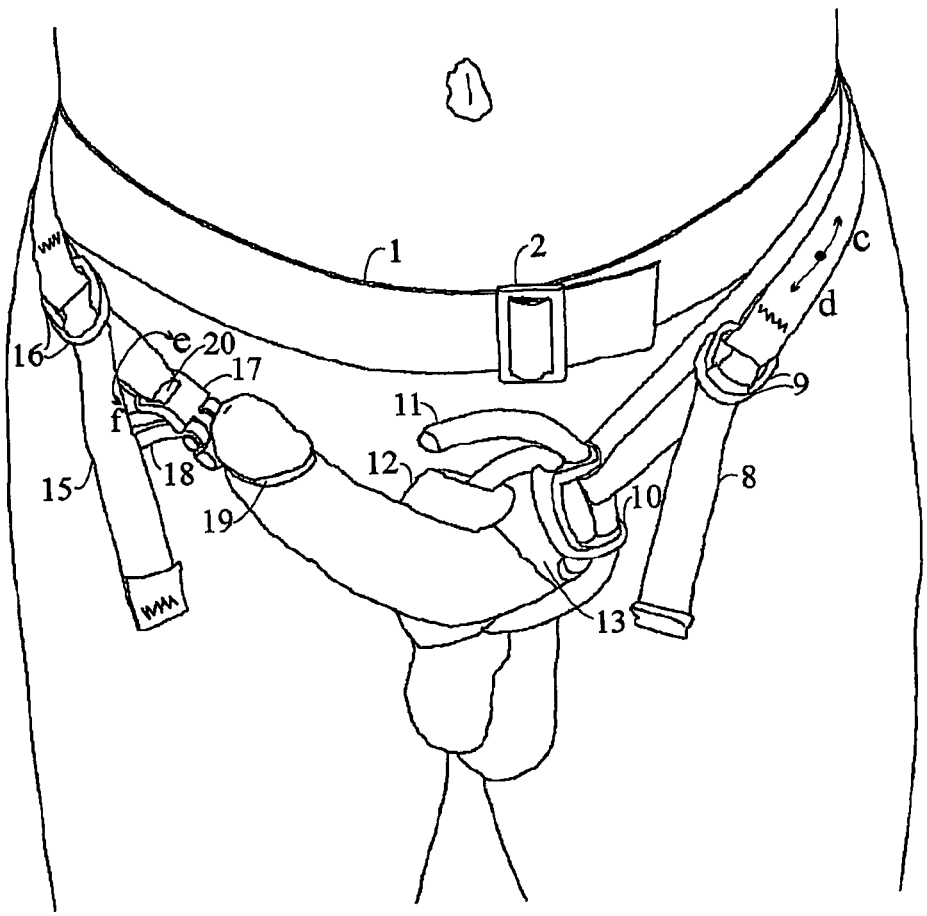
FIG. 3 is a view in front elevation of the present invention as worn by a user.
Figure 4:
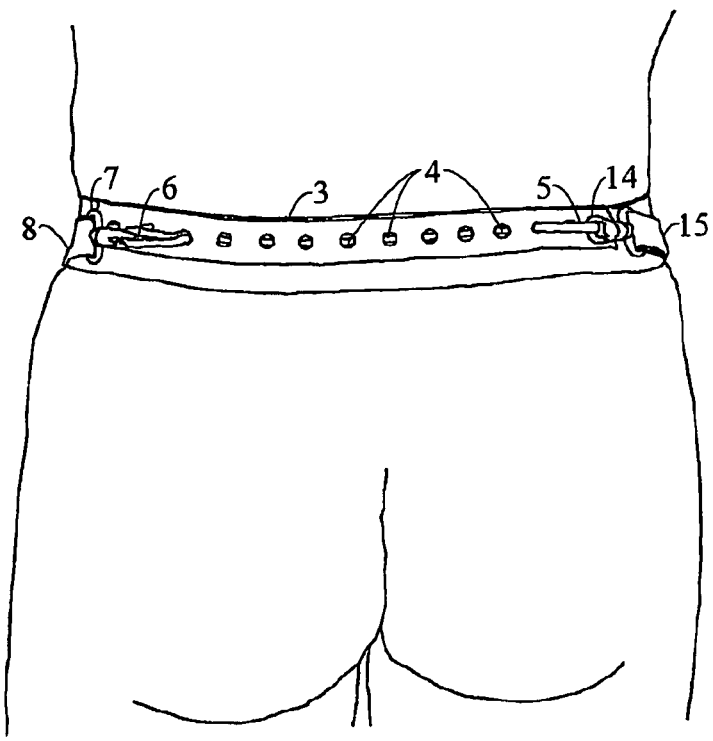
FIG. 4 is a view in rear elevation of the present invention as worn by a user.

Referring now to FIGS. 1-4, the illustrated harness for stretching the penis includes stretchable belt 1, manufactured from mixture of cotton and synthetic fibres or like, having adjusting means 2 for securing around one's waist. Adjusting means 2 can have a vide variety of embodiments. In this preferred embodiment it comprises a simple plastic lightweight buckle. Referring to FIG. 4, unstretchable strong thin string 3 and, over said string, unstretchable strong band with holes 4, both made from synthetic fibres, are attached to the rear outer side of the belt 1, along with the upper edge thereof. String 3 is attached to the belt 1 at three points: at the both left and right ends and at the middle, and said string is pulled out twice i.e. through the two of holes of the band 4 (through which two holes depends on a user's waist size—see FIG. 4) such forming two loops 5 and 6. In loops 5 and 6 are plugged subsystems A and B (see FIG. 2) using small metal rotating snap-hooks 7 and 14 respectively. In accordance with the provided functionality of the present invention and for the sake of easier description three functional parts of the present invention are further signed as belt means subsystem, subsystem A and subsystem B. Subsystem B provides tractive forces to the penis and to the belt 1 in certain directions, while subsystem A provides tractive forces in opposite direction relating to subsystem B to the penis, but also to the belt 1, in order to prevent belt 1 rotation around wearer's waist and consequently loose and total absence of stretching forces. A further object of subsystem A is to provide means for disabling testicles pulling-up under the influence of tractive force, leaving them freely hanging, such preventing any pain arousal and side effects emersion.

Figure 5:
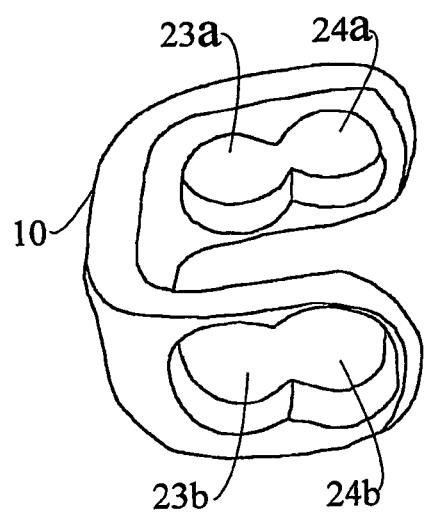
FIG. 5 illustrate a rope regulator means FIG. 6 illustrate a L-shaped connecting member

Subsystem A consist of (see FIG. 2) unstretchable cotton cinching strap 8 having two metal half-rings 9 for strap length adjustment, which said strap upper part is inserted through loop on snap-hook 7 and lower part is inserted around part of the rope 11 which part is threaded through holes 24*a* and 24*b* on rope regulator means 10 (see FIG. 5). Subsystem A further includes said "rope regulator means 10 and said rope 11 with protective pad 12, which rope 11 is threaded through holes 24*a* and 24*b* on rope regulator means 10, thus rope 11 forming in use adjustable loop 13 for penis base abutment.

Figure 6:
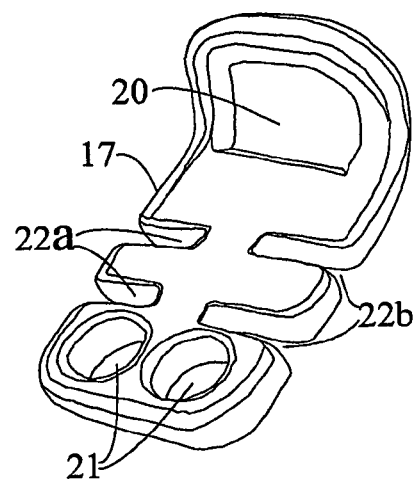

Subsystem B consist of (see FIG. 2) unstretchable cotton cinching strap 15 having two metal half-rings 16 for strap length adjustment, which said strap upper part is inserted through loop on snap-hook 14 and lower part is inserted through U-shaped aperture 20 on L-shaped generally planar connecting member 17 (see FIG. 6). Subsystem B further includes said member 17 having two holes 21, through which holes elastic cord-like member 18 is inserted, thus said cord-like member 18 forming in use adjustable loop 19 for enabling stretching force appliance on the edge of the head of the penis.

Rope 11 is of 9-10 mm diameter and is preferably made of synthetic fibres. Rope regulator means 10 and connecting member 17 are manufactured of heavy-duty unflexible material, under this exemplary embodiment from transparent plastic, but may be also manufactured of metal, woods etc, and both may be partially coated with some thin, soft and skin-cozy material. L-shaped connecting member 17 is, in this preferred embodiment, preferably of the smallest size it can be embodied respective to all of the including constitutive elements and functionality (see FIG. 6). Elastic cord-like member 18 is of 5-6 mm diameter, preferably formed of silicone, but may be manufactured of soft rubber too, and is preferably hose-like (hollow inside), but may be cord-like (full profile).

Referring now to FIG. 2, harness for stretching the penis according to the present invention is shown disassembled on it's subsystems, while in use, first, belt 1 is loosely secured (it is not needed a belt 1 to be firmly tightened since all the forces are applied at it's rear portion to the band 4) around a male's waist using buckle 2, thus that buckle 2 is not placed on the middle of the wearer's body, in order not to interact with eventually present trouser's buckle. Then, the head of the penis (optionally being previously wrapped with 1 or 2 layers of the protective gauze) is inserted through elastic loop 19 formed of elastic cord-like member 18 in conjunction with connecting member 17, whereby cinching strap 15 with snap-hook 14 and half-rings 16 are freely hanging down. Said cord-like member 18 is then cinched around penis next to the penis head, and said cord-like member 18 is finally being fixed using channels 22*a* and 22*b* on said connecting member 17, thus providing fulcrum for stretching force application. After that, in use, subsystem A is being connected by the snap-hook 7 to the belt 1 via loop 5, and penis and subsystem B (being already connected with) together are inserted through rope loop 13, formed of rope regulator means 10, rope 11 and protective pad 12, having said pad 12 placed on the top (dorsal) side of the base of the penis. Further, snap-hook 14 is connected to loop 6 on belt 1 providing the harness for stretching the penis to be ready for use. Finally, cinching straps 8 and 15 are gradually and alternately tightened, until desired tractive force is attained.

Desired angle of torsion of the penis while stretching is provided by strap's 15 lower part gliding along the aperture 20 (in a direction of the arrows e or f, see FIG. 3) which adjustment of the torsion angle is possible due to a U-shape and at the same time L-shape design of aperture 20 (see FIG. 6).

Respecting that the cinching straps 8 and 15 freely glide on its upper parts through loops of the snap-hooks 7 and 14 respectively, and said straps freely glide on its lower parts through part of the rope 11 and through aperture 20 on connecting member 17 respectively, it is very easy to place pairs of half-rings 9 and 16 respectively (by in-one-point traction of said strap's side next to the wearer's body or that strap's second side carrying half rings, where traction is realised either in a direction of the arrow c or in a direction of the arrow d, see FIG. 3) in a place on one's body where said half-rings are easiest to manage and hence to adjust stretching forces, even over the clothing, and even while walking.

Fast and easy unplugging of snap-hooks 7 and 14, which hold on subsystems A and B to the belt 1, from loops 5 and 6, and replacement of the positions of said snap-hooks and consequently said subsystems provides fast and easy alternation of one's body side where penis is settled, meaning that the penis is stretched while settled in left or in right groin groove, all of this towards better comfortability of the harness and towards side-effects preventing.

While preferred embodiment of the present invention have been shown and described, various modifications may be made without departing from the scope of the present invention, and all such equivalents and modifications are intended to be covered.

I claim as my invention:

1. A harness for stretching the penis, the harness comprising:
    a belt for encircling the waist of the user;
    a fastening mechanism secured to a rear part of the belt;
    a first tractive means for application of tractive forces at the base of the penis of a user of the harness, the first tractive means being releasably securable to the belt at one of a plurality of positions via the fastening mechanism;
    a second tractive means for application of tractive forces at the edge of the head of the penis of a user of the harness, the second tractive means being releasably securable to the belt at one of a plurality of positions via the fastening mechanism;
    whereby the first tractive means and the second tractive means are configured to apply in use a stretching force to the penis of the user of the harness.

2. A harness in accordance with claim 1, wherein the fastening mechanism comprises first and second string loops, the first tractive means being releasably securable to the first string loop and the second tractive means being releasably securable to the second string.

3. A harness in accordance with claim 2, wherein the string loops are adjustably secured via a holed portion of the belt.

4. A harness in accordance with claim 3 further comprising a string element attached to the belt, wherein each string loop is formed by a portion of the string element being pulled through a respective hole of the holed portion.

5. A harness in accordance with claim 4, wherein end portions and a middle portion of the string element are attached to the belt.

6. A harness in accordance with claim 4, wherein the holed portion comprises a plurality of holes for providing said plurality of positions.

7. A harness in accordance with claim 2, wherein the first and second tractive means comprise respective cinching straps adapted and constructed to be releasably secured to the respective string loops.

8. A harness in accordance with claim 7, wherein each cinching strap is releasably secured to the respective string loops by a respective snap hook.

9. A harness in accordance with claim 2, wherein the first and second string loops are adjustably secured to the belt.

10. A harness in accordance with claim 1, wherein the first and second tractive means are adjustable in length to facilitate varying stretching force.

11. A harness in accordance with claim 1, wherein the first tractive means comprises a flexible and slightly extensible cord-like member forming an adjustable loop for encircling around the penis next to the edge of the penis head and hence for enabling tractive force appliance thereto.

12. A harness in accordance with claim 1, wherein the second tractive means comprises:
- an adjustable-length rope forming a penis base abutment loop;
- a rope regulator adapted and constructed to vary the length of the loop; and
- a pad surrounding at least a portion of the loop.

13. A harness in accordance with claim 1, wherein the second tractive means comprises a single U-shaped rigid member having a pair of U-branches with respective, slightly overlapping holes, the holes being adapted to receive a rope.

14. A harness for stretching the penis, the harness comprising:
- a belt for encircling the waist of the user;
- a fastening mechanism secured to a rear part of the belt;
- a first tractive means for application of tractive forces at the base of the penis of a user of the harness, the first tractive means being secured to the belt via the fastening mechanism said first tractive means further comprising a single rigid planar L-shaped rigid member, the L-shaped member having a shorter portion having an aperture adapted to receive a cinching strap, and a longer portion having a pair of channels on each of its sides adapted and constructed to receive a cord-like member, and
- a second tractive means for application of tractive forces at the edge of the head of the penis of a user of the harness, the second tractive means being secured to the belt via the fastening mechanism;
- whereby the first tractive means and the second tractive means apply a stretching force to the penis of the user of the harness.

* * * * *